United States Patent
Ji et al.

(10) Patent No.: US 7,498,035 B2
(45) Date of Patent: Mar. 3, 2009

(54) COMPOUNDS OF HYDROPHILIC POLYMER-POLYCARBOXYL OLIGOPEPTIDE AND MEDICINES, MEDICAL COMPOSITE COMPRISING ABOVE COMPOUND AND USE OF ABOVE COMPOUND IN MEDICINES

(75) Inventors: Shishan Ji, Beijing (CN); Dequan Zhu, Beijing (CN)

(73) Assignee: Beijing Jiankai Technology Company, Ltd., Beijing (CN)

( * ) Notice: Subject to any disclaimer, the term of this patent is extended or adjusted under 35 U.S.C. 154(b) by 152 days.

(21) Appl. No.: 10/506,524

(22) PCT Filed: Mar. 5, 2003

(86) PCT No.: PCT/CN03/00164

§ 371 (c)(1),
(2), (4) Date: Mar. 3, 2005

(87) PCT Pub. No.: WO03/074586

PCT Pub. Date: Sep. 12, 2003

(65) Prior Publication Data

US 2005/0147617 A1 Jul. 7, 2005

(30) Foreign Application Priority Data

Mar. 5, 2002 (CN) .................. 02 1 06691

(51) Int. Cl.
*A61K 39/00* (2006.01)
(52) U.S. Cl. ................. 424/181.1; 514/2; 424/130.1
(58) Field of Classification Search .............. None
See application file for complete search history.

(56) References Cited

U.S. PATENT DOCUMENTS 5,879,923 A * 3/1999 Hirokazu et al.
2002/0009426 A1 * 1/2002 Greenwald et al. ....... 424/78.18

FOREIGN PATENT DOCUMENTS

EP 1580216 * 9/2005
WO WO-01/57067 * 8/2001
WO WO-03/101476 * 12/2003

OTHER PUBLICATIONS

Solomons, et al., Organic Chemistry, 2004, John Wiley & Sons., 3 pages.*
[Retrieved from] http://web.archive.org/web/20000414203748/http://members.aol.com/logan20/outline1.html, 2000, 4 Pages, [Retrieved on Jul. 6, 2007].*
Communication pursuant to Article 157(2)(a) EPC corresponding to European application 03 711 787.6-2115 Dated Oct. 8, 2006.*
Communication pursuant to Article 96(2) EPC corresponding to European application No. 03 711 787.6-1216 dated May 12, 2006.*
English Language Abstract of JP60096605A2: Production of Hydrophilic Resin to Mitsubishi (May 30, 1985).*

* cited by examiner

*Primary Examiner*—Andrew D Kosar
*Assistant Examiner*—Satyanarayana R Gudibande
(74) *Attorney, Agent, or Firm*—Jenkins, Wilson, Taylor & Hunt, P.A.

(57) ABSTRACT

The present invention relates to a conjugate of hydrophilic polymer-multicarboxyl oligopeptide and drug molecule of the following formula:

$$P-X-(NH-CH-\overset{\overset{O}{\|}}{C})_m-Z-TA$$
$$\underset{\underset{\underset{TA}{|}}{\underset{Z}{|}}}{\underset{C=O}{|}}{(CHR_i)_j}$$

wherein: P is a hydrophilic polymer; m is an integer of 2~12; j is an integer of 1~6; $R_i$ is a group selected from H, $C_{1-12}$ alkyl, substituted aryl, aralkyl, heteroalkyl and substituted alkyl; X and Z are linking groups; and TA is drug molecule. The conjugate has low toxicity and an ability to carry more than one drug molecule to improve solubility, sustain and control drug release, and has a remarkably enhancing effect especially to antitumor drug such as paclitaxel and camptothecin etc.

3 Claims, 3 Drawing Sheets methoxylpolyethylene glycol-glutamic acid oligopeptide

COMPOUNDS OF HYDROPHILIC POLYMER-POLYCARBOXYL OLIGOPEPTIDE AND MEDICINES, MEDICAL COMPOSITE COMPRISING ABOVE COMPOUND AND USE OF ABOVE COMPOUND IN MEDICINES

FIELDS OF THE INVENTION

The present invention relates to a new conjugate of hydrophilic polymer-multicarboxyl oligopeptide and drug molecule, a pharmaceutical composition comprising the conjugate and the pharmaceutical use of the conjugate.

BACKGROUND OF THE INVENTION

Among the active constituents of nature medicine, proteins, polypeptides, terpenoids, steroids, alkaloids, flavonoids, anthraquinones, and phenylpropanoid phenols all show various effective properties in the term of biologically activity, and therefore, they've been widely used in medicine. Their glycoside, nucleoside and polypeptide derivatives have also shown considerable applications. As natural active constituents, they have the advantages of fast biodegradation rate, little or no residue, low toxicity, and little or no side effects. However, they still have some disadvantages such as low bioavailability, short physiological half-life, poor water solubility, immunogenecity and the like.

To solve the problems, the derivatives of PEG have been widely used to conjugate with proteins, peptides or other therapeutic agents in order to prolong their physiological half-life and to lower their immunogenicity and toxicity. Clinically, PEG and its derivatives have been widely used as carrier to manufacture preparations of commercial drugs. And the attempt of conjugating PEG to drug molecule has an impressive progress in the last 10 years and has been applied to many officially approved drugs. For example, PEG-intron®, a conjugate of PEG and α-interferon, exhibits longer circulation half-life and better therapeutic effect compared to the native form of α-interferon. It has been shown that the conjugate of PEG and paclitaxel correspondingly reduces the toxicity and prolongs the bioactivity. The metabolism processes of these conjugate are well known, showing that PEG is a safe drug modifier.

When conjugating PEG to drugs, often is used a process called as PEGylation, in which one or two of the terminal groups of PEG are chemically activated to have a proper functional group which is reactive to at least one functional group of the drug to form a stable bond. This stable bond can be eliminated by degradation under proper conditions in vivo, and thereby the active ingredient is released.

It's reported that PEG can be used to conjugate to many drugs. The prodrugs of PEG derivatives conjugating with paclitaxel have been disclosed in U.S. Pat. Nos. 5,824,701 and 5,840,900 and CN patent CN1283643. In these patents, each of the two terminal groups of PEG is conjugated with a paclitaxel molecule. In order to increase the drug molecule load, U.S. Pat. No. 6,153,655 discloses a terminally branched PEG structure, in which two functional groups are formed via amino linkage at the two termini of PEG. However, the introduction of non-biological branched small molecule also makes the drug property indefinite. U.S. Pat. Nos. 5,977,163 and 6,262,107 and Chinese patent CN1164533 disclose a paclitaxel prodrug with polyglutamic acid as carrier, in which paclitaxel is attached randomly to the active carboxyl groups of glutamic acid along the polyglutamic acid skeleton. The broad polydispersity and uncertainty of the toxicity of polyglutamic acid limit the application of these inventions.

SUMMARY OF THE INVENTION

Therefore, the object of the present invention is to provide a conjugate of the hydrophilic polymer-multicarboxyl oligopeptide and drug molecule represented by the following formula:

$$P-X-(NH-CH-\overset{O}{\overset{\|}{C}})_m-Z-TA$$
$$|$$
$$(CHR_i)_j$$
$$|$$
$$C=O$$
$$|$$
$$Z$$
$$|$$
$$TA$$

wherein:
P is a hydrophilic polymer;
m is an integer from 2 to 12;
j is an integer from 1 to 6;
$R_i$ is a group selected from the group consisting of H, $C_{1-12}$ alkyl, substituted aryl, aralkyl, heteroalkyl and substituted alkyl;
X is a linking group;
Z is a linking group selected from O and NH; and
TA is a drug molecule.

According to another aspect of the invention, there is provided a pharmaceutical composition comprising the above conjugate as active ingredient.

According to still another aspect of the invention, there is provided a use of the above conjugate in preparing a pharmaceutical composition.

The conjugate of the present invention can improve the absorption of drugs, prolong therapeutic duration, increase therapeutic effect, reduce dosage, and avoid toxicity and other side effects.

BRIEF DESCRIPTION OF THE DRAWINGS

The following is a more detailed description of the present invention by referring to the following drawings, in which.

DETAILED DESCRIPTION OF THE INVENTION

Figure 1:
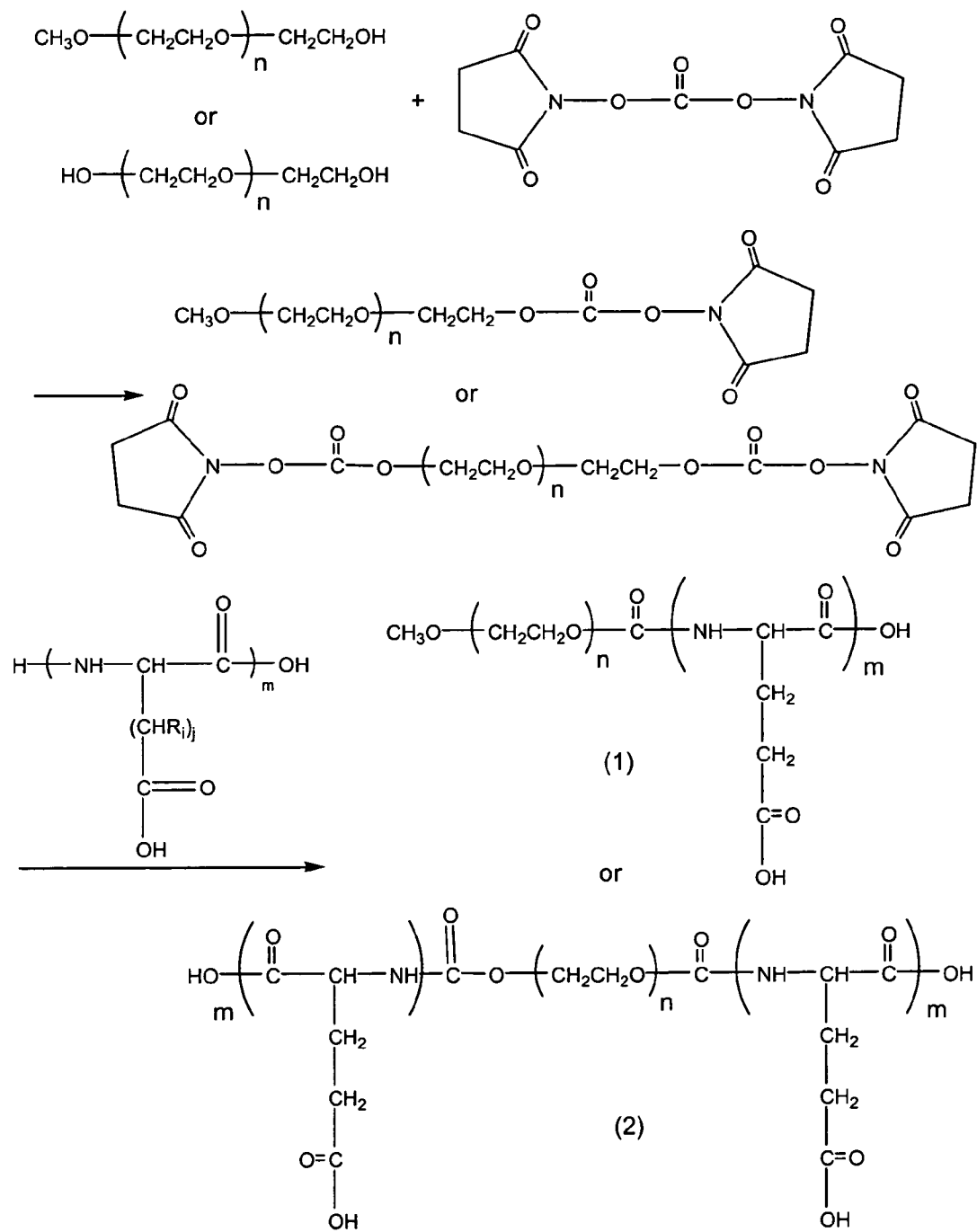
FIG. 1 shows the synthesis of PEG-glutamic acid oligopeptide derivatives.

The hydrophilic polymer used in the conjugate of the present invention is, for example, polyethylene glycol, polypropylene, polyvinyl alcohol, polyacrylmorpholine or copolymer thereof, among them, polyethylene glycol and its copolymer are preferable. Acidic oligopeptide of amino acid, especially oligopeptide of glutamic acid is conjugated to the parent polymer by modifying free end hydroxyl of such hydrophilic polymer. This conjugation provides linking sites between the polymer and drug molecule. In this way, free amino and hydroxyl of proteins, peptides or other the active ingredients of nature medicine can be linked to the polymer.

Especially for the active ingredient of small molecule nature medicine, one or more drug molecules can be linked to the hydrophilic polymer-multicarboxyl oligopeptide by this way in order to ensure an appropriate drug concentration and sustained release.

In the conjugate according to the present invention, multicarboxyl groups of glutamic acid oligopeptide provide many conjugation sites, and the conjugate thus has a higher drug load than the usual linear PEG carrier. The difference between glutamic acid oligopeptide and polyglutamic acid is that glutamic acid oligopeptide has a definite numbers of active carboxyl groups per oligopeptide chain. Therefore, when conjugating with drug molecule such as paclitaxel, it will be easy to confirm and repeat the loading amount of the drug. At the same time, because of non-hydrophilicity of the drugs such as paclitaxel, the conjugate of hydrophilic polymer-glutamic acid oligopeptide-drug molecule will form a molecular micelle/microsphere structure consisting of a number of aggregating molecules in aqueous solution. This structure will maintain the favorable properties of the hydrophilic polymer, such as hydrophilicity, flexibility, and anti-macrophage phagocytosis. Meanwhile, the structure provides sustained release of the drug molecule and prolonged retention time in vivo for the drug, especially nature medicines.

One of the advantages of the present invention is that, in addition of the characteristics of the hydrophilic polymer such as PEG or its derivatives, for example, solubility, non-immunogenicity and non-toxicity, the oligopeptide groups provide many loading sites for the drug molecules, to ensure the effective blood concentration and the stepwise release of the drug.

Now we'll take PEG derivatives as an example to explain the linkage between hydrophilic polymer and multicarboxyl oligopeptides.

The structure of PEG derivatives includes the polymeric branched chain part and the terminal functional group part, which are described respectively as follows.

Polyethylene glycols (PEGs) are represented by the following general formula below:

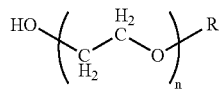

wherein:
R is H or $C_{1-12}$ alkyl; and
n is an integer, representing the degree of polymerization.

As a lower alkyl, R can be any lower alkyl group having 1-6 carbon atoms, for examples, methyl, ethyl, n-propyl, iso-propyl, n-butyl, iso-butyl, n-pentyl, and n-hexyl. As a cycloalkyl, R is preferably a cycloalkyl containing 3-7 carbon atoms, for example, cyclopropyl, cyclobutyl, and cyclohexyl. Among those, cyclohexyl is more preferable. The typical compound is methoxy-polyethylene glycol (mPEG). Other analogs and derivatives of polyethylene glycol, such as polypropylene glycols, polyvinyl alcohols, and polyacrylmorpholines and the like, can also be used in the present invention.

In respect of PEGs, they are usually measured by molecular weight. It's preferred the molecular weight of PEG which forms the conjugate falls in the range from 300 to 60000 Daltons, which means n is about 6~1300. It's more preferred that n is 28, 112 and 450, respectively corresponding to molecular weight of 1325, 5000, and 20000. Because of the potential non-homogeneity of the starting PEGs which are usually defined by their molecular weights rather than the self-repeating unit n, PEGs are normally characterized with average weight molecular weight, instead that PEGs are characterized with their slelf-repeating units represented by n. The starting PEG compounds with different molecular weights are readily synthesized using the known methods of the art or are commercially available.

The multicarboxyl oligopeptides are represented by the following general formula:

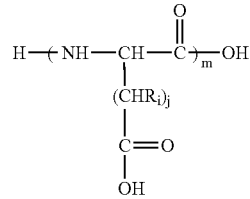

wherein:
m is an integer of 2~12, representing the degree of polymerization;
j is an integer of 1~6; and
$R_i$ is a group selected from the group consisting of H, $C_{1-12}$ alkyl, substituted aryl, aralkyl, heteroalkyl and substituted alkyl.

As a lower alkyl, $R_i$ can be any lower alkyl group having 1-12 carbon atoms, for example, methyl, ethyl, n-propyl, iso-propyl, n-butyl, iso-butyl, n-pentyl and n-hexyl, and possible cycloalkyl. As an aralkyl, $R_i$ is preferably benzyl or phenylethyl. The preferred substituted aryl is benzyl.

The synthesis of oligopeptide may be carried out according to the general synthesis method. With protective amino acid, amino acid polymer can be produced with high yield under the effect of dehydrant. Of course, because the oligopeptide of the present invention is a homo-polypeptide, there's no structural sequence problem here. Therefore, easier methods can be used herein, such as mixed acid anhydrides method, active ester method and N-carboxy-a-amino acid anhydrides (NCA) method etc.

Taking N-carboxy-a-amino acid anhydrides method as an example, the synthesis is shown as follows:

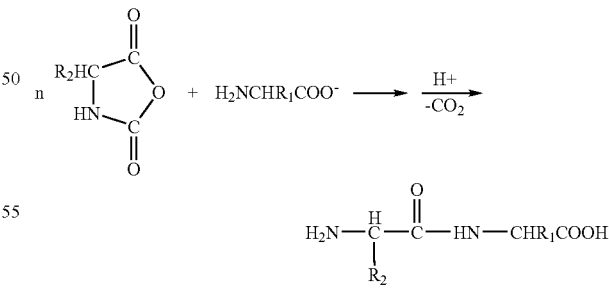

The reaction has the advantages of fast reaction speed and short synthesis cycle. When the reaction is complete, the obtained peptides with free amino group can be used directly in the next synthesis step of oligopeptides without separation. The side chain generally needs less protection. Side chain protection is usually necessary for the side chain of NCA. For amino component, only the side chains of lysine and cysteine need to be protected.

Multicarboxyl-oligopeptide compound are readily synthesized using known methods in the art or are commercially available.

The hydrophilic polymer-glutamic acid oligopeptide moiety of the present invention is synthesized from hydrophilic polymer and glutamic acid oligopeptide by the known methods of the art.

In practical application, the terminal groups of the hydrophilic polymer need to be activated to ensure that it is capable of reacting with amino or carboxyl groups of the oligopeptide to form the conjugated. In respect of the intended use, the terminal functional groups can be modified with the following methods:

a. Amination. The amino that is of greater reactivity takes the place of hydroxyl after the hydrophilic polymer is aminated. It's especially important when the polymer reacts with a molecule comprising carboxylic acid group to yield a conjugate.

b. Carboxylation. Carboxylating the hydrophilic polymer improves its reactivity, and makes it capable of conjugating to molecules containing amino or carboxyl groups.

c. Other methods such as modifications by acyl chloride, hydrazine, maleimide, pyridine disulfide etc. can all be appropriately adopted as well.

All of the methods listed above will lead to the formation of chemical bonds between the functional groups of hydrophilic polymer and oligopeptide. Thus it's possible to make good use of the advantages of the two compounds.

All of the drugs used at present, especially nature medicines, comprise functional groups such as amino, carboxyl and hydroxyl groups. In vivo, these functional groups can conjugate with monosaccharide, polysaccharide, nucleoside, polynucleoside, and phosphoryl etc to form structure pharmacologically active in vivo.

Consequently, hydrophilic polymer-multioligopeptide can conjugate to the drug molecules in the same way to replace bio-organic molecules and overcome their shortcomings of short physiological half-time and short therapeutic duration. The hydrophilic polymer-multicarboxy oligopeptide of the present invention has the following formula:

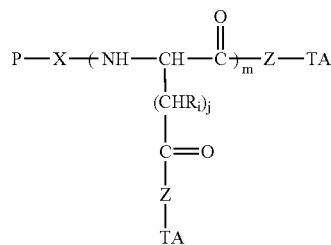

wherein:
P is a hydrophilic polymer, which may be polyethylene glycol, polypropylene glycol, polyvinyl alcohol, polyacrylmorpholine or their copolymer, and polyethylene glycol and its copolymer are preferred;
m is an integer of 2~12;
j is an integer of 1~6;
$R_i$ is a group selected from the group consisting of H, $C_{1-12}$ alkyl, substituted aryl, aralkyl, heteroalkyl and substituted alkyl;
X is a linking group, preferably $(CH_2)_i$, $(CH_2)_iOCO$, $(CH_2)_iNHCO$ and $(CH_2)_iCO$, wherein i is an integer of 1~10;
Z is a linking group selected from O and NH; and
TA is a drug molecule.

If the hydrophilic polymer comprises free hydroxyl groups, the hydroxyl groups can be blocked by $C_{1-12}$ alkoxyl, cycloalkoxyl or aroxyl, preferably by methoxyl, ethoxyl, isopropoxyl, cyclopropoxyl, cyclobutoxyl, cyclohexoxyl or benzoxyl.

Additionally, target molecule, such as antibody etc., can be linked to the hydrophilic polymer to targetedly deliver the conjugate of the present invention.

Hydrophilic polymer can be conjugated to drug molecule through esterification reaction. This process can be simply represented as follows:

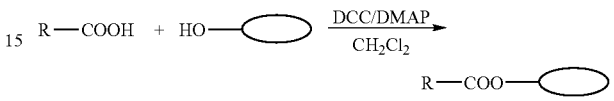

Ester group can be eliminated by biodegradation in vivo to release the active ingredient.

According to the present invention, the drug part of the conjugate can be any appropriate drug molecule including, for example, amino acids, proteins, enzymes, nucleosides, saccharides, organic acids, glycosides, flavonoids, quinones, terpenoids, phenylpropanoid phenols, steroids and glycosides thereof, alkaloids and the like.

Preferably, the drug molecule included in the conjugates of the present invention is the active ingredient separated from nature plants, such as cinobufagin, clycyrrhetinic acid and scopoletin. Particularly preferably, the drug molecule is the ingredient of nature medicine used in the treatment of tumor, such as paclitaxel, camptothecin, hydroxylcamptothecin, etoposide and the derivatives thereof.

The conjugate of the present invention can be administered in the form of pure compounds or pharmaceutically acceptable compositions via any acceptable administration route or being included in the reagent that has the similar use. Thus, the conjugate can be administered by oral, nasal, parenteral, topical, transdermal or rectal routes in the dosage form of solid, semisolid, freeze dried powder or liquid, such as tablets, suppositories, pills, soft and hard gelatin capsules, powders, solutions, suspensions and aerosols. The unit dosage forms suitable for a precise-dosage and easy administration are preferable. The composition includes conventional pharmaceutical carrier or excipient and the conjugate as active ingredient (one or more). The composition may also include other medical agents, carrier and adjuvant.

Generally, depending on the desired administration way, pharmaceutically acceptable composition includes about 1-99 wt. % of the conjugate of the present invention, and 99-1 wt. % of the pharmaceutically suitable excipient. Preferably, the composition includes 5-75 wt. % of the conjugate and the rest is pharmaceutically suitable excipient.

The composition which may be administered in the form of liquid such as solution and suspension can be prepared by dissolving or dispersing the conjugate of the present invention (about 0.5-20%) and the optional pharmaceutical adjuvant into carrier. Examples of the carrier for forming solution or suspension include water, saline, aqueous glucose, glycerol, ethanol and the like.

If needed, the composition of the present invention can further include some additives such as wetting agent, emulsifier, pH buffer, and antioxidant etc, for example citric acid, sorbitan monolaurate, triethanolamine oleate, butylated hydroxytoluene and the like.

The practical preparation methods of such dosage forms are known or obvious to the technician in the art, for example referring to Ramington's Pharmaceutical Sciences, 18$^{th}$ edition, (Mack Publishing Company, Easton, Pa., 1990). In any case, according to the techniques of the present invention, the used composition includes an effective amount of the conjugate according to the present invention to treat corresponding diseases.

EXAMPLES

The conjugate of the present invention and its preparation method will be further described by referring to the following examples. However, these examples do not intend to limit the scope of the invention by any means. The scope of the present invention is restricted only by the claims.

Example 1

Preparation of Methoxypolyethylene Glycol-glutamic Acid Oligopeptide (1)

FIG. 1 shows the synthesis method thereof. 10 g of methoxypolyethylene glycol (molecular weight is 5000) and 2 g of N,N'-disuccinimidyl carbonate were dissolved in 100 ml of acetonitrile, and 0.5 ml of dry pyridine were added thereto. Reaction mixture was stirred overnight at room temperature under the protection of nitrogen. Excess solvents were removed by rotary evaporation and the residue was dried under vacuum. The obtained solid was added into 20 ml of dry dichloromethane, and the mixture was filtered to remove the undissolved. The organic layer was washed once with sodium acetate buffer solution (0.1 M, pH 5.5), dried with anhydrous sodium sulfate, and concentrated. The product was transferred with ether, filtered and dried under vacuum. Yield: 9.0 g (90%). NMR (DMSO): 3.5 (br m, Hs of PEG), 3.24(3H, s), 4.45(2H, t), 2.82(4H, s).

0.6 g dipeptide of glutamic acid (Glu-Glu) was dissolved in 50 ml phosphate buffer solution (0.1 M, pH 7.4), and 4 g of methoxypolyethylene glycol succinimidyl carbonate (molecular weight 5000, prepared in the former step) were added thereto. The solution was stirred for 6 hours at room temperature and extracted 3 times with dichloromethane. The combined organic phase was dried with anhydrous sodium sulfate. The solvent was removed by rotary evaporation under reduced pressure. The residue was added in 100 ml isopropyl alcohol, and filtered. The product was dried under vacuum and purified by ion-exchange chromatography. Yield: 3.6 g (90%). NMR (DMSO): 3.5 (br m, Hs in PEG), 3.24(3H, s), 4.41 (2H, t), 2.32 (4H, t).

Example 2

Preparation of Polyethylene Glycol-diglutamic Acid Oligopeptide (2)

FIG. 1 shows the synthesis method thereof. 30 g of polyethylene glycol (molecular weight 35,000) and 2 g of N,N'-disuccinimidyl carbonate were dissolved in 200 ml of acetonitrile, and 0.5 ml dry pyridine was added thereto. Reaction mixture was stirred overnight at room temperature under the protection of nitrogen gas. Excess solvent was removed by rotary evaporation and the residue was dried under vacuum. The obtained solid was added into 50 ml of dry dichloromethane and the mixture was filtered to remove the undissolved. The organic layer was washed once with sodium acetate buffer (0.1 M, pH 5.5), dried with anhydrous sodium sulfate, and concentrated. The product was transferred by ether, filtered, and dried under vacuum. Yield: 27.2 g (90%). NMR (DMSO): 3.5 (br m, Hs of PEG,), 4.45 (4H, t), 2.82 (8H, s).

0.1 g of dipeptide of glutamic acid (Glu-Glu) was dissolved in 20 ml of dimethylformamide, and 10 g of polyethylene glycol disuccinimidyl carbonate prepared above (molecular weight 35000) were added to the solution. Reaction mixture was stirred for 6 hours at room temperature. Solid precipitate was filtered off. The residue solution was precipitated with 100 ml isopropyl alcohol, filtered, and dried under vacuum. The product was purified with ion-exchange chromatography. Yield: 4.2 g (40%). NMR (DMSO): 3.5 (br m, Hs of PEG), 4.41(4H, t), 2.37(4H, s), 2.32 (4H, t).

Example 3

Preparation of the Conjugate of Methoxypolyethylene Glycol-glutamic Acid Oligopeptide and Paclitaxel (3)

Figure 2:
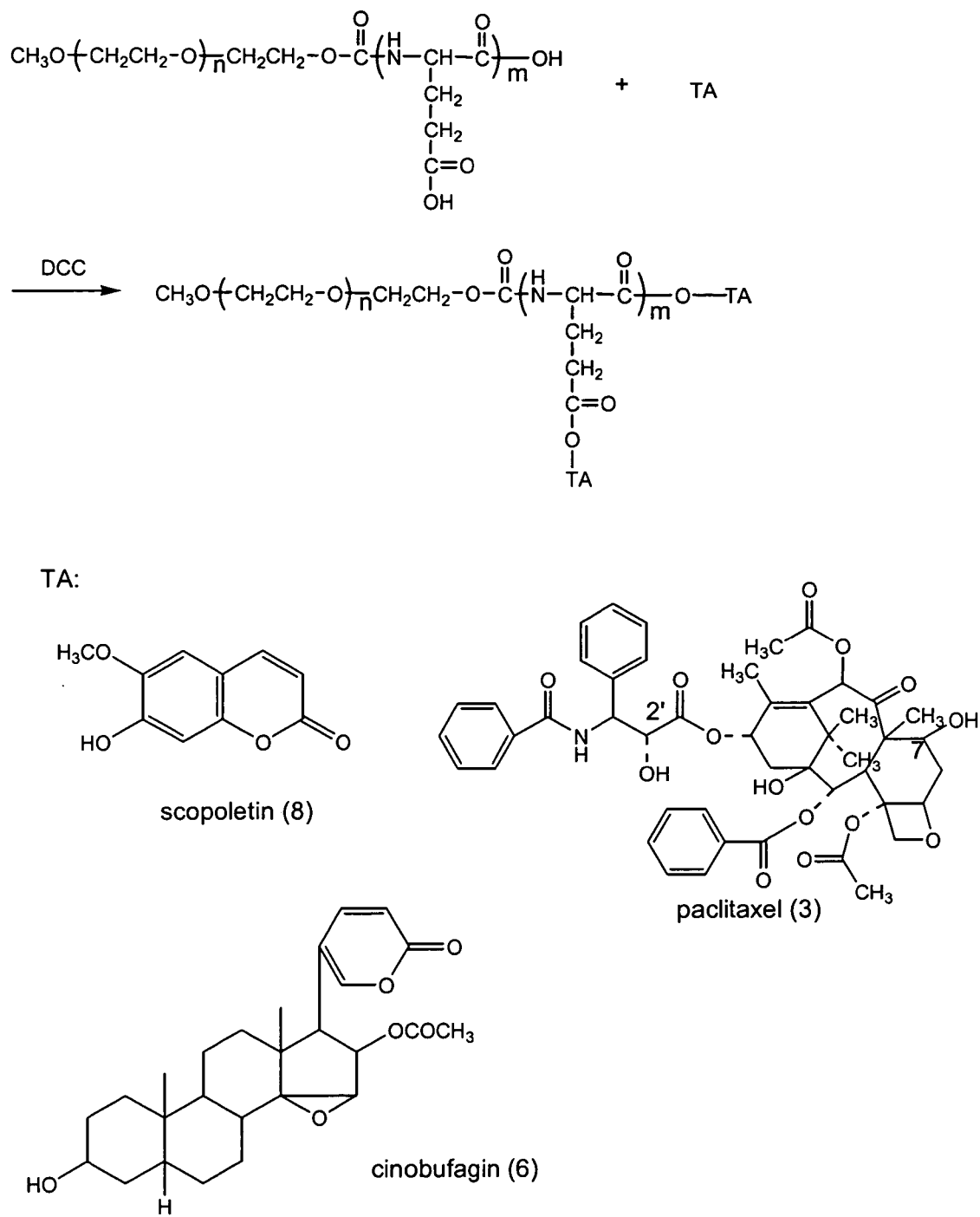
FIG. 2 shows the synthesis of ester bonding conjugates of PEG-glutamic acid oligopeptide derivatives and drugs.

FIG. 2 shows the synthesis method thereof. 1.25 g of methoxypolyethylene glycol diglutamic acid dipeptide prepared in Example 1, 0.7 g of paclitaxel, and 0.1 g of 4-dimethylamino pyridine (DMAP) were dissolved into 15 ml of dry dichloromethane, and 0.2 g of dicyclohexylcarbodiimide (DCC) was added thereto. The reaction mixture was stirred overnight at room temperature under the protection of nitrogen gas. Excess solvent was removed by rotary evaporation and the residue was dissolved into 8 ml of 1,4-dioxane. The mixture was filtered to remove the precipitate and the solution was concentrated. 30 ml of isopropyl alcohol were added to the residue, filtered, and dried under vacuum. Yield: 1.6 g (80%). M.p.: 59~62° C.

Example 4

The Preparation of the Conjugate of Polyethylene Glycol-glutamic Acid Oligopeptide and Paclitaxel (4)

4.0 g of polyethylene glycol diglutamic acid dipeptide prepared in Example 2, 0.4 g of paclitaxel and 0.08 g of 4-dimethylamino pyridine (DMAP) were dissolved into 20 ml of dry dichloromethane. After that, 0.15 g of dicyclohexylcarbodiimide (DCC) were added thereto. Reaction mixture was stirred overnight at room temperature under the protection of nitrogen gas, and the excess solvent was removed by rotary evaporation. The residue was dissolved in 10 ml of 1,4-dioxane, filtered to remove precipitate and the mother liquid was concentrated. The residue was added to 50 ml of isopropyl alcohol, and filtered off. The product was dried under vacuum. Yield: 3.7 g (85%). M.p.: 61-64° C.

Example 5

Preparation of the Conjugate of Methoxypolyethylene Glycol-glutamic Acid Peptide and Camptothecin (5)

Figure 3:
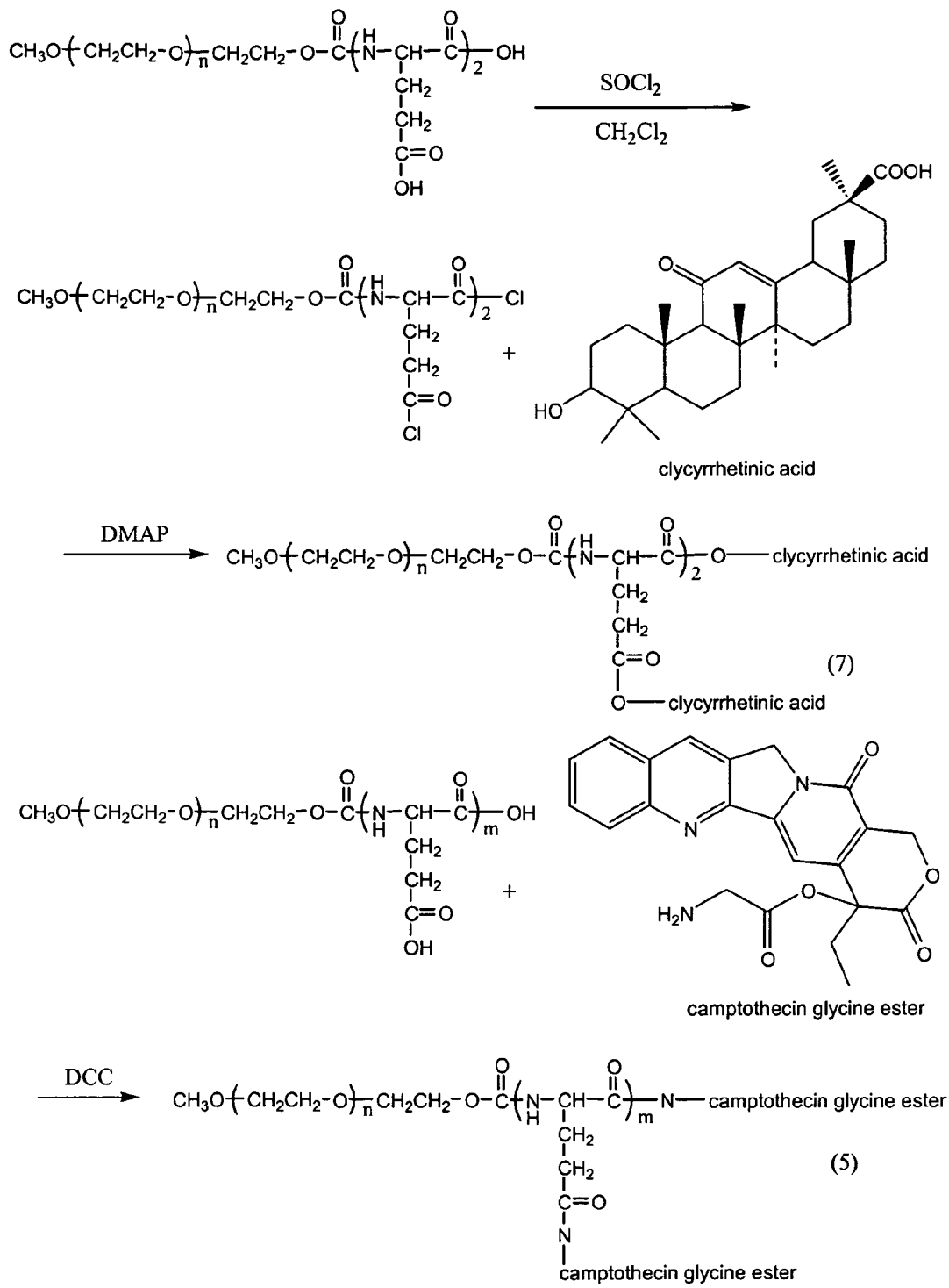
FIG. 3 shows the synthesis of other kind of conjugates of PEG-glutamic acid oligopeptide derivatives and drugs.

FIG. 3 shows the synthesis thereof. 0.7 g of camptothecin and 0.5 g of N-tert-butyoxylcarboxylglycine (BOC-gly) were dissolved in 10 ml of dry dichloromethane. 0.62 g of dicyclohexylcarbodiimide (DCC) and 0.36 g of 4-dimethylamino pyridine (DMAP) were added thereafter. The reaction mixture was stirred overnight at room temperature. The solid formed during reaction was filtered out and the mother liquid was concentrated under reduced pressure. The mixture was added into 50 ml ether and filtered off. The precipitate was collected and dried under vacuum.

0.5 g of camptothecin N-tert-butyoxylcarboxylglycine ester (obtained in the former step) was dissolved in 10 ml chloroform. Then, 10 ml trifluoroacetic acid was added. The reaction mixture was stirred for 5 hours at room temperature and concentrated under reduced pressure, and then 50 ml of diethyl ether were added. The precipitate was collected by filtering and dried under vacuum.

2.5 g of methoxylpolyethylene glycol glutamic acid dipeptide prepared in Example 1, 0.6 g of substituted camptothecin (prepared in the former step), and 0.2 g of 4-dimexylamino pyridine (DMAP) were dissolved in 30 ml of dry dichloromethane. 0.4 g of dicyclocarbodiimide (DCC) was then added. The reaction mixture was stirred overnight at room temperature under the protection of nitrogen gas. Excess solvent was removed by rotary evaporation, and the residue was dissolved in 15 ml of 1,4-dioxane. Precipitation was filtered off and the mother liquid was concentrated. The residue was added to 50 ml isopropyl alcohol and filtered off. The obtained solid was dried under vacuum. Product can be purified by ion-exchange chromatography. Yield: 2.5 g (80%). M.p: 60-63° C.

Example 6

Preparation of the Conjugate of Methoxylpolyethylene Glycol-glutamic Acid Oligopeptide and Cinobufagin (6)

FIG. 2 shows the synthesis thereof. 1 g of methoxylpolyethylene glycol glutamic acid dipeptide prepared in Example 1 were dissolved in 10 ml of dichloromethane. 60 mg of cinobufagin, 32 mg of 4-dimethylamino pyridine (DMAP) and 40 mg of dicyclohexylcarbodiimide (DCC) were then added. The reaction mixture was stirred overnight at room temperature under the protection of nitrogen gas. The excess solvent was removed by rotary evaporation. The residue was dissolved in 20 ml of 1,4-dioxane, filtered off and the mother liquid was concentrated. The residue was added into 100 ml isopropyl alcohol and filtered off. The obtained solid product was dried under vacuum. Yield: 0.8 g (60%). M.p: 58~80° C.

Example 7

Preparation of the Conjugate of Methoxylpolyethylene Glycol-glutamic Acid Oligopeptide and Clycyrrhetinic Acid FIG. 3 shows the synthesis thereof. 1 g of methoxylpolyethylene glycol glutamic acid dipeptide prepared in Example 1 were dissolved in 10 ml dichloromethane. 0.2 ml thionyl chloride was added thereto dropwise. The reaction mixture was stirred for 2 hours. Solvent and impurities with low boiling point were removed by distillation under reduced pressure. A solution of 70 mg clycyrrhetinic acid in 10 ml dichloromethane was added and dissolved by stirring. 60 mg of 4-dimethylamino pyridine (DMAP) were then added. The reaction solution was stirred for 12 hours at room temperature under the protection of nitrogen gas. The solvent was concentrated under vacuum. The residue was added into 20 ml isopropyl alcohol and filtered. The precipitate was collected, washed with diethyl ether, dried by suction, and further dried under vacuum. The product can be purified by ion-exchange chromatography. Yield: 0.8 g (60%). M.p: 60~62° C.

Example 8

Preparation of the Conjugate of Methoxylpolyethylene Glycol-glutamic Acid Oligopeptide and Scopoletin (8)

FIG. 2 shows the synthesis thereof. 5 g of methoxylpolyethylene glycol glutamic acid dipeptide prepared in Example 1 were dissolved in 50 ml of dichloromethane. 0.70 g of scopoletin, 0.1 g of 4-dimethylamino pyridine (DMAP), and 0.82 g of dicyclohexylcarbodiimide (DCC) were then added. The reaction mixture was stirred for 12 hours at room temperature under the protection of nitrogen gas. The solvent was concentrated under vacuum. The residue was added to 20 ml of 1,4-dioxane, and filtered. The precipitate was collected, washed with ether and dried by suction. The mother liquid was evaporated under reduced pressure. 100 ml isopropyl alcohol was added to the residue. The precipitate was collected, washed with diethyl ether and dried by vacuum. The precipitates were combined and dried under vacuum. Yield: 4 g (80%). M.p: 58~61° C.

Example 9

This example is to explain the preparation process of a typical parenteral composition. The composition comprises the conjugate of the present invention.

| Component | |
|---|---|
| Conjugate prepared in Example 3 | 2 g |
| 0.9% saline | to 100 ml |

The conjugate prepared in Example 3 was dissolved in 0.9% saline to obtain 100 ml solution for intravenous injection, which was filtered through 0.2 μm membrane and packed sterile.

What is claimed is:
1. A conjugate of methoxylpolyethylene glycol-glutamic acid oligopeptide and drug molecule having the following formula:

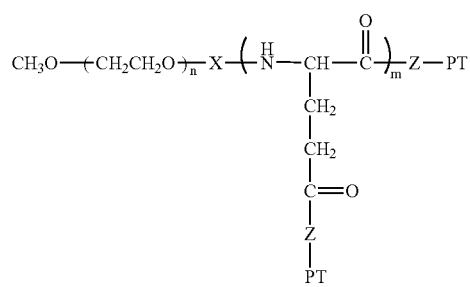

wherein:
n is an integer from 10-1200;
m is an integer from 2-12;
X is a linking group selected from the group consisting of $(CH_2)_i$, $(CH_2)_iOCO$, $(CH_2)_iNHCO$ and $(CH_2)_iCO$, and wherein i is an integer from 0-10 inclusive;
Z is a linking group selected from O and NH; and PT is a drug molecule selected from the group consisting of paclitaxel, camptothecin, cinobufagin, clycyrrhetinic acid, scopoletin and esters thereof.

2. A composition comprising a conjugate according to claim 1 and a pharmaceutically acceptable carrier or excipient.

3. The composition of claim 2, wherein the composition is formulated into a form selected from the group consisting of a tablet, a suppository, a pill, a soft gelatin capsule, a hard gelatin capsule, a powder, a solution, a suspension, and an aerosol.

* * * * *